United States Patent [19]

Small et al.

[11] 4,252,644

[45] Feb. 24, 1981

[54] HIGH PERFORMANCE ION EXCHANGE COMPOSITION AND THE REMOVAL AND SEPARATION OF IONS THEREWITH

[75] Inventors: Hamish Small; Timothy S. Stevens, both of Midland, Mich.

[73] Assignee: The Dow Chemical Company, Midland, Mich.

[21] Appl. No.: 42,674

[22] Filed: May 25, 1979

Related U.S. Application Data

[60] Continuation of Ser. No. 566,569, Apr. 9, 1975, abandoned, which is a division of Ser. No. 402,669, Oct. 2, 1973, abandoned.

[51] Int. Cl.³ .............................................. B01D 15/08
[52] U.S. Cl. .................................. 210/656; 210/685; 210/686
[58] Field of Search ........................... 55/67, 197, 386; 210/31 C, 36, 198 C; 521/28, 29, 32; 210/37–38

[56] References Cited

U.S. PATENT DOCUMENTS

| | | | |
|---|---|---|---|
| 3,485,658 | 12/1969 | Iler | 428/308 |
| 3,488,922 | 1/1970 | Kirkland | 55/67 |

*Primary Examiner*—Ivars C. Cintins
*Attorney, Agent, or Firm*—David H. Fifield; Douglas N. Deline

[57] ABSTRACT

An ion exchange composition comprising an insoluble substrate of a synthetic resin having ion exchanging sites at least on its available surface; and a finely divided, insoluble material comprising synthetic resin particles of from about 0.1 to about 5 microns median diameter (with respect to volume) having, at least on their outer surfaces, ion exchanging sites which attract the ion exchanging sites of the substrate, irreversibly attached as a monolayer to the available surface of the substrate. The composition is used for removal and separation of ions, and is especially useful in liquid ion exchange chromatography. For example, a chromatographic separation of halide ions is effected with high speed and resolution by contacting an aqueous solution thereof with a bed of the ion exchange composition which consists of surface sulfonated resin beads of a styrene-divinylbenzene copolymer to the surface of which is irreversibly attached a monolayer of quaternary ammonium styrene-divinylbenzene copolymer resin particles in the hydroxy form, and then eluting the bed with an aqueous sodium hydroxide solution.

16 Claims, No Drawings

HIGH PERFORMANCE ION EXCHANGE COMPOSITION AND THE REMOVAL AND SEPARATION OF IONS THEREWITH

This is a continuation of application Ser. No. 566,569 filed Apr. 9, 1975, now abandoned, which in turn is a divisional of application Ser. No. 402,669 filed on Oct. 2, 1973, now abandoned.

BACKGROUND OF THE INVENTION

1. Field of the Invention

The invention pertains to a composition useful in and a process for practicing high performance ion exchange chromatography. Materials for performing high speed liquid chromatographic analyses are known where only the thin outer surface of the chromatographic support materials is available for actively exchanging ions with liquid media.

2. Prior Art:

Parrish, in *Nature* 207:402 (1965), describes "superficial ion exchange chromatography" using beads of crosslinked polystyrene which bear a "shallow surface laye" of ion exchange groups. Horvath et al. describe ion exchange chromatography with glass beads having a styrenedivinylbenzene resin skin, appropriately sulfonated or aminated to produce cation and anion exchange materials which they call "pellicular resins" in reference to the skin-like layer of active sites on these beads. *Analytical Chemistry* 39:1422 (1967).

Iler, in U.S. Pat. No. 3,485,658 (1969), describes the preparation of chromatic materials where alternating layers of colloidal solid particles are laid down on a substrate by treating the substrate, in alternating fashion with dispersions of oppositely charged colloidal particles. These colloidal particles as described are, among others, alumina, silica and ionic synthetic polymers.

Kirkland, in U.S. Pat. No. 3,488,922 (1970), describes a method of "chromatographic separation which uses superficially porous glass beads having sorptively active crusts. " These chromatographic materials consist of a plurality of impervious glass beads which have been alternately coated with monolayers of microparticular ion exchange resins, alumina, silica and the like, using the method described by Iler.

Levendusky, in U.S. Pat. No. 3,250,702 (1966), describes the production of an ion exchange bed where particles of about equal size of both anionic and cationic resins are allowed to agglomerate or clump together to form the bed. The particles described therein are larger than about 400 mesh (about 35 microns).

Grubhofer, in German Auslegeschrift 1,045,978 (1958), describes the preparation of nonagglomerated mixed resin beds where a suspension of anion or cation exchange particles, of about 0.2 millimicrons patticle size, is contacted with one of the components of the mixed resin bed which has a charge opposite to that of the suspension particles, thereby laying down a thin layer of these suspension particles on the particles (500–1000 microns) of that component.

In U.S. Pat. No. 2,961,417 (1960), Small describes a method for avoiding agglomeration of a mixed resin bed by treatment of either the cationic or anionic resin particles with resinous polyelectrolyte solutions. Iler likewise mentions that strong electrolytes redisperse the colloidal particles from his substrate surfaces.

SUMMARY OF THE INVENTION

The invention is an ion exchange composition comprising:

Component A, an insoluble substrate comprising a synthetic resin having ion exchanging sites, at least on its available surface; and Component B, a finely divided, insoluble material comprising synthetic resin particles of from about 0.1 to about 5 microns median diameter, having ion exchanging sites, at least on their outer surfaces, which attract available sites of Component A, irreversibly attached as a monolayer to the available surface of Component A.

The invention is further directed to a process for removing ions of like charge from a solution thereof, said process comprising contacting the solution with the novel ion exchanging composition having ion exchanging sites at least on the outer surfaces of Component B particles which attract said ions. In a preferred embodiment, ions of like charge are chromatographically separated in a process comprising: (a) passing a fluid mixture comprising the ions through a bed comprising the novel ion exchange composition which has ion exchanging sites at least on the outer surfaces of Component B particles which attract at least one of said ions; and (b) eluting the bed with an eluent which differentially removes the attracted ions from the bed.

The ion exchanging sites on Component A may be cation or anion exchanging sites and the sites of Component B may also be either cation or anion exchanging sites selected to attract available sites on Component A. Cation exchanging sites on either component may be chelating sites which are attracted to or capable of forming coordination complexes with the ion exchanging sites of the other component.

The ion exchange composition of the invention has advantages over materials described in the prior art in that it may be utilized in strongly basic media which cause silica substrates and silane bonds to disintegrate. Also, the irreversibly attached monolayer is not displaced by strong electrolyte and polyelectrolyte solutions as would be expected.

DETAILED DESCRIPTION OF THE INVENTION

Substrate:

The invention composition comprises a substrate hereinafter designated Component A, comprising a synthetic resin material chosen to be insoluble in any solvent system with which it may be later contacted. It may be utilized in any shape, form or size and is preferably comprised of finely divided particles of about 5 to about 100 microns particle size, most preferably of about 35 to about 75 microns. When Component A is utilized in the finely divided particulate form, the particles are preferably substantially spherical in shape.

The synthetic resin material from which Component A will be derived is suitably any synthetic resin material having ion exchanging sites at least on its available surface (hereinafter "available sites"). For example, synthetic ion exchange resins such as polyacrylic, polymethacrylic, poly(vinylaromatic), polyphenol-formaldehyde resins, and the like which are suitably crosslinked to render them insoluble in the solvent media with which they will be contacted, and which have desired ion exchanging sites are suitable materials from which Component A may be derived. Synthetic resins employed may be the macroporous type or the gel type resins well known in the art.

The term "available surface," as used herein, means that surface of Component A which will come into contact with particles of Component B when Component A is contacted with a suspension of Component B. For example, when Component A is made from beads of a gel type resin, the available surface area will be essentially the outer surface of those beads. When Component A is made from a macroporous resin, the available surface will be both the outer surface of that resin and the inner surface of the minute channels which permeate the structure of the resin and which have pore sizes greater than the particle size of Component B.

In a preferred embodiment of the invention, Component A comprises about 400 to 200 mesh (about 35–75 microns) beads of cross-linked poly(vinylaromatic) resin, most preferably a styrene-divinylbenzene copolymer containing about 2% to about 8% divinylbenzene monomer by weight, of the gel type which have anion or cation exchanging sites on their available surface.

Monolayer:

The ion exchanging composition of the invention further comprises a finely divided solid material, hereinafter referred to as Component B, comprising synthetic resin particles of from about 0.1 to about 5 microns median diameter, wherein the particles of Component B form an irreversibly attached monolayer on the available surface of Component A. These particles have ion exchanging sites which attract the available sites of Component A. Again, the material from which these particles are derived should be chosen so as to be insoluble in the solvents with which they will be contacted.

Suitable materials from which the particles may be derived are the well-known synthetic polymeric ion exchange resins mentioned in the description of Component A above and may be of the gel or macroporous resin type. Preferred for use in Component B are poly(vinylaromatic) resins; most preferred is a cross-linked styrenedivinylbenzene copolymer having a ion exchanging sites substantially throughout the entirety of a majority of the particles.

The ion exchanging sites which are found at least on the outer surfaces of Component B particles, preferably substantially throughout the entirety of a majority of the particles, may be anion or cation exchanging sites depending upon the type of available sites found on Component A. When the available sites of Component A are anion exchanging sites, the sites of Component B will be cation exchanging sites and vice versa. The term "cation exchanging sites" is meant to include chelating sites which are attracted to or form coordination complexes with the ion exchanging sites of the other component. For example, aminocarboxylic acid groups are such chelating sites. The preparation of resins with such chelating sites is well known in the art, for example, as described by Morris, U.S. Pat. No. 2,875,162 (1959), and Mock et al., U.S. Pat. No. 2,910,445 (1959). Such a chelating resin, commercially available, is Dowex A-1 chelating resin.

As mentioned above, Component B will comprise particles preferably of from about 0.1 about 5 microns median diameter. Most preferably, the particles will be of from about 0.6 to about 1.8 microns median diameter. The term "median diameter" as used herein is a figure which relates to the statistical distribution of total particle volume with respect to varying particle size. While the term may be defined by an involved mathematical treatment, we find it easier to graphically treat experimental data on particle size distribution in terms of volume to determine a median diameter for a sample of Component B particles. A more detailed treatment of this subject is given in Examples 8–11, below. Also described there is a term "diameter range" which describes the range of particle sizes, the volume of which makes up about 90% of the total volume of Component B particles as they are applied to the substrate.

Utilizing this information concerning particle size and volume distribution, a sample of Component B particles may by selected to give ion exchange compositions with different useful characteristics. Generally, where particle samples with a large median diameter are employed, an ion exchange composition is produced with high capacity and low performance relative to an ion exchange composition prepared from a particle sample with a relatively smaller mean diameter. Optimum ranges of median diameters and diameter ranges are described more fully in Examples 8–11.

Preparation:

The novel ion exchange composition is prepared by irreversibly attaching a monolayer of Component B particles to the available surface of Component A. This may be accomplished by contacting a liquid suspension of Component B particles with the available surface of Component A. By testing for the presence of Component B particles in the suspension after it has been thoroughly contacted with Component A, one determines when substantially all the available sites of Component A have been attached by Component B particles.

Since the novel ion exchange composition is ordinarily employed in a conventional ion exchange column, it is conveniently formed in situ by choosing Component A to be beads of a commercially available ion exchange resin, slurrying the beads in a nonsolvent liquid, packing this slurry in the ion exchange column and then passing the suspension of Component B particles through the column. By continuously monitoring the column effluent stream for breakthrough of Component B particles, the completion of formation of the irreversibly attached monolayer is determined once substantially all of Component A available sites have been attached by Component B particles.

When the monolayer has been irreversibly attached to Component A, the composition is washed with suitable quantities of the nonsolvent liquid to remove excess Component B particles. The ion exchange composition is ready for operation and may be used without further treatment. Where desired, the ion exchange composition may be separated from the liquid, drained and dried at room temperature, for the purpose of storage, transportation and the like.

The term "irreversibly attached," as used herein means that a substantial number of particles of Component B will not be displaced from the available surface of Component A by solutions of strong electrolytes or polyelectrolytes, for example, about a 0.5 molar sodium hydroxide solution, nor by shearing forces such as those encountered when a liquid is passed through an ion exchange bed at elevated flow rates on the order of about 460 ml./hr. in a column of 2.8 mm. internal diameter.

To use Component A or Component B in a smaller particle size than is readily available, the available materials may be reduced in size by conventionally known mechanical means such as ball mills, rod mills and the like. Selection of particles of a suitable size range for use in the invention may be also accomplished by well-known means such as screening through conventional sieves, suspending and settling in a liquid medium by centrifugation or similar means or combinations thereof. Ordinarily, commercially available ion exchange resin beads are suitable for use as Component A. Commercial ion exchange resins with opposite ion exchanging sites may be finely divided by the means described above to form Component B particles. In most instances, aqueous suspensions of Component B or latices thereof are conveniently contacted with Component A in the preparation of the invention composition.

The nature of the ion exchanging sites on each component will be determined by the ultimate use for which an ion exchange composition will be employed. Two main categories of ion exchanging sites are anion and cation exchanging sites. These are further divided in the art into strong and weak base anion exchanging sites and strong and weak acid and chelating cation exchanging sites. Chelating sites have been described above. Strong base anion exchanging sites are generally quaternary ammonium groups while weak base anion exchanging sites are generally tertiary, secondary and primary amine functional groups. Strong acid cation exchanging sites are generally sulfonate functional groups and weak acid cation exchanging sites are generally carboxyl functional groups. Ion exchange resins which contain these functional groups are known, respectively, as strong base and weak base anion exchange resins, and strong acid and weak acid cation exchange resins. Those with chelating sites are known as chelating resins.

In the ion exchange composition of the invention, the two components may comprise any combination of two oppositely charged ion exchange resins. Preferred, however, are combinations of: strong acid-strong base resins; strong acid-weak base resins; strong base-weak acid resins; and strong base-chelating resins. A highly preferred combination is one where Component A comprises a strong acid resin and Component B comprises a strong or weak base resin. A most preferred combination is where Component A comprises a surface sulfonated poly(vinylaromatic) gel type resin and Component B comprises a strong base poly(vinylaromatic) resin having anion exchanging sites substantially throughout the entirety of a majority of the particles.

Ion Exchange Process:

The ion exchange compositions of the invention may be used to remove ions of like charge from a solution by contacting such a solution with the invention composition which has ion exchanging sites, at least on the outer surfaces of Component B particles, which attract the ions to be removed from solution. Such removal is accomplished conveniently by contacting the ion exchange composition with the solution by any conventional means, for example, by slurrying the ion exchange composition with the solution and then physically separating the composition and solution. Removal may similarly be accomplished by passing the solution through a bed of the ion exchange composition to effect the necessary contact. Regeneration of the ion exchange composition may be carried out by contacting it with suitable ion exchange regenerants known in the art.

As noted before, Components A and B are selected such that the ion exchanging sites, at least on the outer surfaces, of Component B particle are sites which exchange their associated ions for the ions which are to be removed from solution. For example, a solution of alkali metal cations will be contacted with an ion exchange composition which has cation exchanging sites at least on the outer surfaces of Component B particles and which has available anion exchanging sites on Component A. Preferably, Component B has cation exchanging sites substantially throughout the entirety of a majority of the particles.

In a preferred embodiment of the invention, the process is carried out by contacting the solution from which ions are to be removed with an ion exchange composition wherein Component A comprises finely divided particles of about 5 to about 100 microns particle size. Also preferred is a process employing an anion exchange composition wherein Component B particles comprise an ion exchange resin with suitable ion exchanging sites substantially throughout the entirety of a majority of the particles.

Chromatographic Separation:

In a chromatographic separation, a mixture of materials to be separated is passed through a separation zone where the passage of the various materials through that zone is differentially retarded by chromatographically active sites. This differential retardation of the various materials results in a separation and resolution thereof upon passage through such a zone.

Ion exchange chromatography is a form of chromatographic separation where a mixture of ions is resolved by contacting that mixture with a material which has available ion exchanging sites capable of exchanging ions for one or more of the ions in the mixture. Separations are commonly carried out by passing the mixture to be resolved through a column which contains the ion exchanging material. Repeated interaction of the available ion exchanging sites with the various ions of the mixture results in a separation of the ions of different chemical types due to the different degrees of attraction exhibited by the ion exchanging sites for the different types of ions.

In order to remove the ions which would otherwise be held by the ion exchanging sites of the column, an eluent which is also attracted by the ion exchanging site is passed through the column, either simultaneously with or after the mixture of ions, in order to "push" the ions through the column so that they may be collected or analyzed as they come off the other end. Such eluents will conveniently be liquid solutions of an ionic material which will regenerate the ion exchanging site to their original form, i.e., $H^+$, $OH^-$, and the like. These eluents are normally selected so that the eluent ion which has the same charge as those ions to be resolved is of a different chemical type than any of those ions to be resolved for convenience in any subsequent analysis of the resolved ions.

The ion exchange composition of the invention has been found to be extremely useful in ion exchange chromatography because of the high performance of this composition in such chromatography. By "high performance" is meant that a high degree and rapid speed of resolution is obtained by using a bed of this composition as the ion exchanging medium with traditional ion exchange chromatography methods. A process employing the ion exchange composition for chromatographic separation of ions of like charge therefore comprises: (a) passing a mixture comprising the ions through a bed comprising the ion exchange composition of the invention which has ion exchanging sites at least on the outer surface of Component B that attract at least one of said ions; and (b) eluting the bed with an eluent which differentially removes the attracted ions from the bed. Preferably, Component B particles also have ion exchanging sites substantially throughout the entirety of a majority of the particles to give an ion exchange composition of useful capacity.

In a preferred embodiment, the mixture to be resolved comprises a liquid solution of the ions. Further preferred embodiments of the process include using a composition in which Component A comprises finely divided particles of about 5 to about 100 microns particle size with Component B particles of from about 0.1 micron and about 5 microns median diameter, most preferably of from about 0.6 micron to about 1.8 micron median diameter.

The ion exchange resin materials used in preparing the ion exchange composition for this chromatographic separation are those described above for preparation of the novel compositions. Preferred combinations of Component A and Component B ion exchanging sites for the process are, respectively: anion exchanging sites-cation exchanging sites where ions separated thereby are cations; anion exchanging sites-chelating sites attracted thereto where the ions separated thereby are cations; and cation exchanging sites-anion exchanging sites where the ions separated thereby are anions. An especially preferred process for separating anions comprises contacting a mixture comprising the ions through a bed of an ion exchange composition wherein Component A comprises finely divided particles of about 35-75 microns particle size whose ion exchanging sites are strong acid cation exchanging sites and Component B particles are of from about 0.1-5 microns median diameter with ion exchanging sites which are strong base anion exchanging sites. In one most preferred process, the Component B particles are of from about 0.6-1.8 microns median diameter and in another have ion exchanging sites substantially throughout the entirety of a majority of the particles.

The eluent to be employed in the chromatographic separation process will depend on the nature of the ions to be separated. Eluents for use in chromatographic separations are well known in the art and include materials such as strong inorganic acids and bases, for example, solutions of hydrochloric acid, sulfuric acid, phosphoric acid, perchloric acid, nitric acid, sodium hydroxide, potassium hydroxide and the like. Solutions of strongly dissociated organic compounds may also be employed, for example, phenates, alkoxides, carboxylic acid salts, amine salts, quaternary ammonium and pyridinium compounds and the like.

The above examples are not meant to be restrictive of the useful eluent systems. One skilled in the art will be able to select suitable eluent systems depending on the type of ion exchange composition and species to be analyzed.

SPECIFIC EMBODIMENT OF THE INVENTION

In the following examples, the particle size of Component A particles has been determined by screening the commercially available ion exchange beads through a conventional sieve to give particles of an average particle size falling within the stated distribution range.

Surface sulfonated styrene-DVB resin beads of the desired particle size were prepared utilizing beads of a styrene-DVB copolymer, about 2-16 wt. % DVB monomer, and treating according to the method described by Small in *Jour. Inorg. Nucl. Chem.* 18:232 (1961). This method involves briefly heating the copolymer with an excess of concentrated sulfuric acid at about 100° C. for about a minute and yields a resin bead with a thin surface shell of sulfonic acid groups which serves as the substrate, Component A, in Examples 2-4 and 6-11 and 13.

With regard to the size of Component B particles, a number of variations were used in applying the particles to the substrate. In Examples 6 and 7, Component B particles were applied as particles of anion exchange latices. These latices were prepared by heating about a 17 wt. % polyvinylbenzyl chloride latex with about 1 wt. % ethylene diamine to cross-link the latex. The cross-linked latex was then treated with trimethylamine to produce what will be referred to as Latex #1 or treated with dimethylethanolamine to produce Latex #2. The diameter ranges of these latices were determined by drying a drop of a treated cross-linked latex (Latex #1 or #2) on a transmission electron microscopy grid, photomicrographing the grid bearing the dried particles on an RCA-G transmission electron microscope and then measuring the distribution of particle sizes on a Quantimet 720 image analyzer. This determined the Martin's diameter, i.e., the longest unbroken horizontal chord, of each particle on the grid. The size range, about 0.06 to about 0.12 micron for both Latex #1 and #2, is the range within which the Martin's diameters of the particles were found to fall.

In Examples 1 through 5, conventional ion exchange resins were ground in a mortar and pestle to a fine powder. This powder was then suspended in distilled water and the suspension allowed to stand about 15 hours. The supernate was decanted, filtered through a fluted Whatman paper and the filtrate was collected and used as obtained to irreversibly attach a monolayer of Component B particles to the substrate by contacting therewith. Exact particle size was unknown but roughly estimated by viewing the powder and sedimentation rates to be in the range of about 0.2 to about 0.5 microns.

In Examples 8 through 11 and 13, compositions were prepared having Component B particles which were obtained by grinding beads of a conventional gel type resin, Dowex 2X8 anion exchange resin, of about 300-850 microns particle size, for about seven days in a small ceramic ball mill. The finely ground resin was then suspended in distilled water and allowed to stand for one hour, the supernate being decanted at that time. This supernate, hereafter Original Supernate, was refined, generally by settling and by progressively more severe centrifugation steps to obtain separate fractions, some of which were then contacted with a given substrate to irreversibly attach the monolayer of Component B particles to the substrate. This sedimentation process is shown in Table I which follows Examples 8-11.

The fractions which were employed in the examples were analyzed by drying a drop of supernate or resuspended sediment, photomicrographing and using an image analyzer in the same manner that was utilized for measuring the latex particles.

The ion exchange resins utilized in the following experience were commercially available materials sold under the following brand names:

Dowex 1X8 anion exchange resin, a trimethylammonium gel type styrene-divinylbenzene (DVB) copolymer containing about 8 wt. % of DVB monomer;

Dowex 2X8 anion exchange resin, a dimethyl hydroxyethylammonium gel type styrene-DVB copolymer containing about 8 wt. % of DVB monomer;

Dowex MSC-1 cation exchange resin, a sulfonated, macroporous, highly cross-linked styrene-DVB copolymer;

Dowex 50WX8 cation exchange resin and Dowex 50WX16 cation exchange resin, surface sulfonated gel type styrene-DVB copolymers containing about 8 wt. % and 16 wt. %, respectively, of DVB monomer; all manufactured and sold by The Dow Chemical Company;

Zipax SAX anion exchanger, an anion exchange material manufactured and sold by E. I. duPont de Nemours & Company and believed to be comprised of a silica bead substrate having a plurality of monolayers laid down on its outer surface and having anion exchanging groups attached thereto by silane linkages;

AS-Pellionex SAX anion pellicular exchange packing, an anion exchange material sold by H. Reeve Anel & Company and believed to be comprised of a substrate having a polymer skin bearing anion exchanging sites.

Example 1:

Cationic Exchanging Composition and Chromatographic Separation Therewith of Lithium, Sodium and Potassium Ions An aqueous slurry of Dowex 1X8 anion exchange resin beads in the chloride form of about 35 to about 75 microns particle size was packed in a 2.8×300 mm. glass column. The outlet of this column was connected to the inlet of another column of the same size which also contained packing of Dowex 1X8 anion exchange resin beads, in the hydroxy form. The outlet of the second column was then connected to a conductivity cell-conductivity meter-recorder combination to measure the conductivity of the effluent stream passing from the second column.

The inlet of the first column was then connected to a sample injection valve and this valve was connected to a pump. An aqueous solution of 0.01 M hydrochloric acid was pumped through this apparatus train at a flow rate of 60 ml./hr. A 0.01 ml. sample of a solution of lithium chloride, sodium chloride and potassium chloride was then injected into the flowing HCl eluent at the head of the first column and about 1.8 minute later a single peak was monitored by the detection-recorder apparatus due to the emergence of lithium hydroxide, sodium hydroxide and potassium hydroxide with no separation of those species being obtained.

The first column was then detached from the apparatus train and a dilute aqueous suspension of finely ground Dowex MSC-1 macroporous cation exchange resin, prepared by grinding the conventional resin in a mortar and pestle as described above, was injected through the column until turbidity could be observed in the effluent from the column, indicating that a monolayer of the finely divided cation exchange resin particles had been irreversibly attached to the beads of the anion exchange resin. This first column's inlet was then attached to the sample injection valve and 0.01 M HCl was pumped through for about 10 minutes at 60 ml./hr. to wash any excess unattached cation exchange resin particles off the column. The column outlet was then reattached to the inlet of the second column and after some further washing with HCL, another 0.01 ml. sample of the aqueous solution of LiCl, NaCl and KCl was injected at the inlet of the first column into the HCl eluent stream having a flow rate of 60 ml./hr. About 2.1 minutes later recordation of peaks of the eluted cations was observed in the following order and times: $Li^+$ peak at 2.3 minutes, back to base line at 2.6 minutes; $Na^+$ peak at 3 minutes, back to base line at 4 minutes; and $K^+$ peak at 4.6 minutes, back to base line at 7.6 minutes. The degree of resolution between the ions was calculated to be $Na^+:Li^+ = 0.81$ and $K^{30}:Na^{30} = 1.5$.

In the separation process, the second column served as a "stripper" to strip the chloride gegenion of the HCl eluent and of the alkaline metal salts from solution and replace it with hydroxyl ion. In this manner, an aqueous solution of lithium, sodium and potassium hydroxide was monitored by the conductivity cell and avoided a masking effect which would occur if the HCl eluent were present. This "stripper" column may be detached and regenerated from time to time with a strong sodium hydroxide solution or may be replaced with a fresh "stripper" column, as desired.

EXAMPLE 2:

Anion Exchanging Composition and Chromatographic Separation Therewith of Chloride and Sulfate Ions In a manner similar to that of Example 1, a first 2.8×300 mm. column was filled with gel type beads of a styrene-2% DVB copolymer resin, of about 44–53 microns average diameter, which had been surface sulfonated by the method described above. This column was then treated with a suspension of mortar ground Dowex 2X8 anion exchange resin particles, in the chloride form, to form an irreversibly attached monolayer. This column was coupled with a 9×250 mm. stripper column filled with about 35–75 micron average diameter Dowex 50WX8 cation exchange resin beads, in the acid form, and the two columns were flushed with a solution 0.04M in sodium hydroxide and 0.01M in sodium phenate. A 0.01 ml. sample of an aqueous solution containing 258 ppm. sodium chloride and 1847 ppm. sodium sulfate was injected into the hydroxide-phenate eluent stream, having a flow rate of 32 ml./hr., at the head of the first column. About 11.5 minutes later, recordation of peaks of the eluted anions began with $Cl^-$ peak at 12.7 minutes, back to base line at 14 minutes and the $SO_4^{--}$ peak at 20.2 minutes, back to base line at 24 minutes. The degree of resolution between $SO_4^{--}$ and calculated to be 2.9.

EXAMPLE 3:

Separation of Mono-, Di- and Trichloroacetate Ions

On the apparatus described in Example 2, an injection was made of a 0.01 ml. sample of sodium monochloroacetate (MCA), sodium dichloroacetate (DCA) and sodium trichloroacetate (TCA) (0.067M in each species) with the same sodium hydroxide-sodium phenate eluent system at a flow rate of 64 ml./hr. About 5 minutes later, recordation of peaks of the eluted MCA, DCA and TCA anions was observed with the monochloroacetate ion peak at 5.7 minutes, back to base line at 6.2 minutes, the dichloroacetate ion peak at 6.7 minutes, back to base line at 7.5 minutes and the trichloroacetate ion peak at 15.7 minutes, back to base line at 22.5 minutes. The degree of resolution between the ions was calculated to be DCA:MCA = 1.3 and TCA:DCA = 3.

EXAMPLE 4:

Separation of Chloride, Bromide and Iodide Ions

In the same manner as in Example 2 and 3, a 0.01 ml. sample of a solution of sodium chloride, sodium bromide and sodium iodide (0.0067M in each species) was injected onto the apparatus at a flow rate of 64 ml./hr. with the same eluent system. About 1.5 minutes later, recordation of peaks of the eluted chloride, bromide and iodide anions was observed with the $Cl^-$ peak at 2.0 minutes, back to base line at 2.8 minutes, the $Br^-$ peak at 3.2 minutes, back to base line at 4.5 minutes and the $I^-$ peak at 14 minutes, back to base line at 17.7 minutes. The degree of resolution between the ions was calculated to be $Br^-:Cl^- = 1.47$ and $I^-:Br^- = 3.0$.

EXAMPLE 5:

Treatment of Ion Exchange Composition with Electrolytes

In light of the earlier work of Small in preventing the agglomeration of mixed resin beds by treatment with polyelectrolytes, the ion exchange composition prepared in Example 1 by irreversibly attaching a monolayer of finely ground Dowex MSC-1 cation exchange resin particles to Dowex 1X8 anion exchange resin beads was treated with electrolytes in attempts to displace the finely ground cation exchange resin particles. The outlet of the column in which the ion exchange composition was prepared was attached to a spectrophotometer. When the monolayer was originally laid down on the substrate, breakthrough of excess suspended cation exchange resin particles was observed by a marked decrease in light transmitted through the effluent stream, as measured by the spectrophotometer.

When a 0.5M aqueous sodium hydroxide solution was passed through a bed of the prepared ion exchange composition, no decrease in light transmission was measured by the spectrophotometer indicating that the finely ground Dowex MSC-1cation exchange resin particles of the monolayer were not displaced in any substantial number by the strong electrolyte from the Dowex 1X8 anion exchange resin substrate. Similarly, a dilute solution of a cationic polyelectrolyte (a water-soluble polyvinylbenzyl trimethylammonium chloride solution of about 800 ppm. concentration) was unable to displace any measurable quantity of the monolayer particles.

EXAMPLE 6:

Separation of Chloride and Sulfate Anions on Ion Exchange Composition with Monolayer Particles of Latex Particles A 2.8×75 mm. column of surface sulfonated styrene-2 wt. % DVB copolymer beads of about 35-75 microns particle size was set up and Latex #1, described above, was passed down the column to form a monolayer of latex particles irreversibly attached to the substrate. This column was attached to a 2.8×150 mm. stripper column containing beads of Dowex 50X8 cation exchange resin in the acid form of, about 35-75 micron average diameter and the detection-recording apparatus attached. Using a 0.01M sodium hydroxide eluent at a flow rate of 160 ml./hr., a 0.1 ml. sample of an aqueous solution 0.0005M in sodium chloride and 0.001M in sodium sulfate was passed through the two column system. The $Cl^-$ peak was recorded at 0.6 minutes, back to base line at 1.5 minutes, and the $SO_4^{--}$ peak at 3.8 minutes, back to base line at 10 minutes. The degree of resolution between $SO_4^{--}$ and $Cl^-$ was calculated to be 1.7.

EXAMPLE 7:

Separation of Anions on Ion Exchange Composition with Monolayer Particles of Latex Particles Apparatus identical to that of Example 6 was assembled with the exception of the first column. The first column contained a surface sulfonated styrene-DVB copolymer substrate as in Example 6 to the available surface of which was irreversibly attached a monolayer of latex particles by passing Latex #2, described above, down the column. This apparatus was then used to separate a solution of several ions, specifically a 0.1 ml. sample of a solution containing sodium chloride, sodium sulfate, sodium nitrite and sodium nitrate. The concentrations of these species were 0.0003M, 0.002M and 0.001M, respectively. The eluent emplyed was 0.05M sodium hydroxide at a flow rate of 16 ml./hr. The recorded results were: $Cl^-$ peak at 9.4 minutes, back to base line (extrapolated) at 10 minutes; $NO_2^-$ peak at 10.7 minutes, back to base line at 13.5 minutes; $NO_3^-$ peak at 15.6 minutes, back to base line (extrapolated) at 19.3 minutes; and $SO_4^{--}$ peak at 19.5 minutes, back to base line at 30 minutes. The degrees of resolution between species pairs were: $NO_2^-:Cl^- = 0.6$; $NO_3^-$ 1.2; $SO_4^{--}:NO_3^- = 0.5$ and $SO_4^{--}:Cl^- = 1.7$.

EXAMPLES 8-11:

Chromatographic Separation of Chloride and Sulfate Ions on Ion Exchange Compositions with Monolayers of Varied Particle Size In the manner previously described, a monolayer of particles was irreversibly attached to four separate substrates in four columns. In each instance, the substrate was a quantity of surface sulfonated styrene-DVB gel type resin beads of about 45-85 microns particle size, the beads having been surface sulfonated as described above. The monolayers which were irreversibly attached to the substrates in each of the four ion exchange compositions were designed to be of a different particle size range. This was accomplished by utilizing a suspension of particles from a different fraction of the Original Supernate, as obtained by the successive centrifugation steps described earlier and shown in Table I, below.

The fractions utilized were Sediment 1, Sediment 3 and Sediment 6 (all resuspended in distilled water) and Supernate 6. The four columns in which the four different ion exchange compositions were prepared and tested were all 2.8 mm. internal diameter and varied in length due to the different ion exchange capacity of the different compositions. Each column was attached to a 9×300 mm. stripper column packed with beads of Dowex 50WX16 cation exchange resin and a 0.1 ml. sample of a sodium chloride, sodium sulfate solution was pased through each column to determine their relative performances. The sample in Examples 8 and 9 contained 10 ppm. chloride ion and 50 ppm. sulfate ion while the sample in Examples 10 and 11 contained 2 ppm. chloride ion and 10 ppm. sulfate ion. The eluent employed was an aqueous sodium hydroxide-sodium phenate solution which was 0.01M in both sodium hydroxide and sodium phenate in Examples 8 and 9 and which was 0.005M in both in Examples 10 and 11. The particle size for the sediment fractions utilized to form each monolayer was determined from photomicrographs with an image analyzer, as described earlier for Latex #1 and #2.

As mentioned earlier, "median diameter" is a term which relates the statistical distribution of total particle volume of a sample of Component B particles to the particle sizes of that sample. The median diameters of Sediment 1, Sediment 3 and Sediment 6 were determined using the Martin's diameters (D) obtained from photomicrographs of the sediments on the image analyzer described earlier and using number of particles (n) found for each D (in 0.02 micron increments). Each D was cubed and the cube multiplied by n for that D. The product $nD^3$ was then plotted against increasing D on paper of uniform weight and thickness according to the formula $nD^3$ vs. D. The curve described by the formula $nD^3$ vs. D was then cut out and weighed on a microbalance, 5% of the total weight was clipped off each end of the curve by cuts perpendicular to the baseline D, and discarded. By further clipping from one end of the curve and by weighing the portion clipped against the portion of the curve remaining, a point of balance was attained. The median diameter, $D_m$, is therefore defined as the point of intersection of the final cut with the baseline. The median diameters of Sediment 1, Sediment 3 and Sediment 6 were found to be 4.7 microns, 1.8 micron and 0.95 micron, respectively.

The "diameter range" was the range of D, from one end of the curve base line to the other, which remained once the initial 5% of total weight had been clipped from each end of the curve. Diameter range, therefore, describes the range of D within which 90% of the total particle volume falls. Diameter ranges for Sediment 1, Sediment 3 and Sediment 6 were about 1.3 to 6 microns, 0.5 to 3 microns and 0.2 to 1.9 micron, respectively.

Capacity of ion exchange compositions prepared from resin particles of the order of magnitude discussed herein (about 0.01-10 microns) is proportional to the total volume of the Component B particles, $nD^3$. It is preferred that the diameter range of Component B particles sample be such that the lower end of the range is greater than about $D_m/10$ and the upper end of the range is less than about $D\sqrt[3]{10}$ in order to obtain optimum performance from the ion exchange compostions prepared from such samples. While Component B particles samples whose $nD^3$ vs. D plots approximate normal Gaussian curves are preferred, samples having $nD^3$ vs. D plots of bi, tri- or polymodality and diameter ranges within the $D_m/10$ to $D_m\sqrt[3]{10}$ range may suitably be used to prepare the Component B monolayer of the ion exchange composition of the invention.

Since no photomicrograph was obtained of Supernate 6, median diameter and diameter range were estimated by relative comparison of its capacity and performance with those of the other sediment fractions. The median diameter calculated was about 0.6 micron and the diameter range about 0.06–1.3 micron.

From our experiments, we find that Component B particles' median diameter is preferably of from about 0.1 micron to about 5 microns; most preferably of from about 0.6 micron to about 1.8 micron. The diameter range for these particles is suitably about 0.01 micron to about 10 microns, preferably about 0.05 micron to about 5 microns and most preferably about 0.1 micron to about 2 microns.

TABLE I

| Fraction Treated | Treatment of Original Supernate Treatment | Products |
|---|---|---|
| Original Supernate | Centrifuged N = 1500  R = 20 T = 0.17 | Supernate 1; Sediment 1 |
| Supernate 1 | Settled for 18 hours | Supernate 2; Sediment 2 |
| Supernate 2 | Centrifuged N = 2000  R = 20 T = 2 | Supernate 3; Sediment 3 |
| Supernate 3 | Centifuged N = 2000  R = 20 T = 6 | Supernate 4; Sediment 4 |
| Supernate 4 | Centrifuged N = 10,000 R = 10 T = 1 at 20° C. | Supernate 5; Sediment 5 |
| Sediment 5 | Resuspended in distilled water | Suspension 5 |
| Suspension 5 | Centrifuged N = 10,000 R = 10 T = 0.25 at 20° C. | Supernate 6; Sediment 6 |

N = Rotating Velocity in rpm.
R = Rotating Radius in cm.
T = Duration of Centrifugation in hr.

EXAMPLE 12:

Chromatographic Separation on Commercially Available High Performance Resin—ZIPAX SAX Anion Exchanger A comparative separation of chloride and sulfate ions on Zipax SAX anion exchanger beads of about 50 microns diameter was carried out using the 2 ppm. chloride ion and 10 ppm. sulfate ion solution of Examples 10 and 11 with a comparable stripper and eluent system (0.05M sodium hydroxide). Column length and flow rate were different than in Examples 8–11 and the comparative data reported below has been extrapolated from actual data, giving the benefit of any doubt of the Zipax SAX exchanger.

The results of Examples 8–12 are reported below in Table II. Resolution time, as reported is total reslution time less stripper time since the stripper is a dead volume with regard to ion exchange of the pertinent anions.

Further experimentation with Zipax SAX anion exchanger indicated that the pellicule of active ion exchanger was permanently deactivated by basic systems as utilized above. The above data therefore indicates that the Zipax SAX anion exchanger does not operate well under basic conditions but does not imply that the Zipax SAX anion exchanger would not operate properly when used according to manufacturers' directions.

TABLE II

Chromatographic Separation of Chloride and Sulfate Anions on Ion Exchange Compositions with Monolayers of Varied Particle Size

| Ex. No. | Monolayer Particles of: | Median Diameter, Microns | Diameter Range, Microns | Column Length, mm. | Flow Rate ml./hr. | Degree of Resolution $SO_4^=:Cl^-$ | $SO_4^=$ Resolution Time in Minutes** |
|---|---|---|---|---|---|---|---|
| 8 | Sediment 1 | 4.7 | 1.3–6 | 1.5 | 46 | 0.6 | 6 |
| 9 | Sediment 3 | 1.8 | 0.5–3 | 40 | 184 | 1.3 | 10 |
| 10 | Sediment 6 | 0.95 | 0.2–1.9 | 300 | 230 | 3.0 | 5.5 |
| 11 | Supernate 6 | 0.6$^e$ | 0.06–1.3$^e$ | 300 | 230 | 1.2 | 3.0 |
| Separation on a Commercial Packing | | | | | | | |
| 12 | Zipax SAX anion exchanger | Bead size about 50 microns | | 300* | 230* | 0.83* | 0.92* |

$^e$ = Estimated from capacity ratios of Sediment 6 and Supernate 6
\* = Calculated from experimental data obtained under different flow rate and column length
\*\* = Measured Resolution Time including Stripper Time except Ex. No. 12 where Stripper Time is subtracted.

The performance of an ion exchange column is difficult to define in practical terms. Height Equivalent to a Theoretical Plate (HETP) is one factor, but for specific analyses, it does not include selectivity. Degree of resolution (d) includes selectivity and HETP and is a better measure of performance; it ignores, however, the maximum pressure drop the system can take. The above data was obtained at 500 psi. column pressure, the maximum rating of the equipment used.

The data of Table II shows the resolution time (t) and the degree of resolution (d) between chloride and sulfate anions under similar conditions for the different column packings of Examples 8–12. If one wishes to know the relative performances of these packings, one way to compare them is to calculate the time required by each packing to obtain the degree of resolution shown by the packing performing most poorly (in this case, the Sediment 1 ion exchange composition).

To calculate degree of resolution between the ion species, the width of the peak of each ion on the chromatograph was measured between opposite points on the ascending and descending slopes of each peak at a distance half the maximum height of the peak. This width is the "half peak width." The distance between the maxima of the two peaks was measured and divided by the sum of the half peak widths to give the degree of resolution between the two species as known in the art.

The resolution time for the last eluting ion, sulfate in the above examples, is the time required from injection of sample to completely elute the ion, in this case determined by observing the return of the peak curve to base line or by extrapolating the descending slope to base line. Since the use of a stripper column added an extra time increment to resolution time, a true resolution time (t) was calculated by subtracting the time required for the ions being resolved to pass through the stripper column (stripper time) from the measured resolution time. This tended to correct an unfavorable bias against packings with shorter true resolution times, i.e., the Zipax SAX anion exchanger.

Under similar conditions (temperature, pressure, flow rate, eluent, etc.) degree of resolution is proportional to the square root of the length of the column and also proportional to the square root of the true resolution time. This may be represented by the equation $d \propto \sqrt{t}$. By virtue of the relationship $d_2/d_1 = \sqrt{t_2}/\sqrt{t_1}$, the relative performances of the packings in Examples 8–12 may be calculated, with respect to the packing performing most poorly, Sediment 1. The known degree of resolution, $d_1$, and the known true resolution time, $t_1$, are used to calculate the true resolution time, $t_2$, on the same packing which would result if the degree of resolution, $d_2$, were the same as the degree of resolution of the packing to which the performance is to be related, in this case Sediment 1. The comparative results are found in Table III, below.

TABLE III

Relative Performance of the Packings of Examples 8–12

| | | If $d_2$ is | then $t_2$ is |
|---|---|---|---|
| Monolayer of: | Sediment 1 | 0.6 | 4 min. |
| | Sediment 3 | 0.6 | 1.6 min. |
| | Sediment 6 | 0.6 | 0.16 min. |
| | Supernate 6 | 0.6 | 0.45 min. |
| | Zipax SAX anion exchanger | 0.6 | 0.48 min. |

Thus, if we shortened the columns of Examples 9–12 to get 0.6 degree of resolution between sulfate and chloride ions, the true resolution times shown in Table III would be observed. The best performing packing is the one which shows shortest true resolution time where the degree of resolution of all packings is equivalent.

One might postulate that the poorer performing columns could be lengthened to increase the degree of resolution but in that case the flow rates could not be maintained since the apparatus was already operating at maximum pressure of 500 psi.

EXAMPLES 13 and 14

Comparison between Anion Exchange Composition and Commercial AS-PELLIONEX SAX Anion Pellicular Exchange Packing In a similar comparison, a commercial packing AS-Pellionex SAX anion pellicular exchange packing and an anion exchange composition prepared in the manner of Examples 8–11 above from Sediment 4 on surface sulfonated styrene-DVB beads were inserted in comparable apparatus and a sodium chloride-sodium bromide solution 0.01 M in each was eluted at 60 ml./hr. with 0.05 M sodium hydroxide solution. The results were a degree of resolution of bromide and chloride ions of 2.5 for the Sediment 4 anion exchange composition and 2.0 for the AS-Pellionex SAX anion pellicular exchange packing and true resolution times of 7.73 minutes and 5.43 minutes, respectively, for bromide ion. Previous experience with Sediment 4 and Sediment 6 anion exchange compositions allowed the calculation of true resolution time for bromide ions on the Sediment 6 anion exchange composition used in Example 10 above, under the same flow conditions for the given resolution of 2.5. This calculated time was 4.3 minutes. The true resolution time for AS-Pellionex SAX anion pellicular exchange packing for degree of resolution between $Cl^-$ and Br⁻ of 2.5 was therefore calculated to be 8.5 minutes. These results are shown in Table IV below.

TABLE IV

Relative Performance of Packings of Examples 13 and 14 and Sediment 6 Composition

|  |  | $d_1$ | $t_1$ |
|---|---|---|---|
|  |  |  | Minutes |
| Example 13 | Sediment 4 anion exchange composition | 2.5 | 7.73 |
| Example 14 | AS-Pellionex SAX anion pellicular If exchange packing | 2.0<br>$d_2 = 2.5$ | 5.43<br>then $t_2 = 8.5$ |
| — | Sediment 6 anion exchange composition | 2.5* | 4.3* |

*Calculated from the comparable data obtained in Example 13 for the Sediment 4 ion exchange composition.

We claim:

1. A process for chromatographic separation of ions of like charge comprising:
   (a) passing a liquid solution comprising the ions through a bed comprising Component A, an insoluble substrate which consists essentially of synthetic resin, having ion-exchanging sites at least on its available surface; and Component B, a finely-divided, insoluble material comprising synthetic resin particles of from about 0.1 micron to about 5 microns median diameter having, at least on their outer surfaces, ion-exchanging sites which attract available sites of Component A, wherein the particles of Component B are irreversibly attached as a monolayer to the available surface of Component A such that a substantial number of particles of Component B will not be displaced from the available surface of Component A by an aqueous sodium hydroxide solution of about 0.5 molar concentration; and which composition has ion-exchanging sites at least on Component B's outer surface that attract at least one of said ions; and
   (b) eluting the bed with an eluent which differentially removes the attracted ions from the bed.

2. The process of claim 1 wherein Component A of the composition comprises finely divided particles of about 5 to about 100 microns particle size which have ion exchanging sites at least on their available surfaces.

3. The process of claim 2 wherein the particles of Component B have ion exchanging sites substantially throughout the entirety of a majority of the particles.

4. The process of claim 2 wherein Component A particles are of about 35 to about 75 microns particle size.

5. The process of claim 4 wherein Component B particles are of from about 0.6 to about 1.8 micron median diameter.

6. The process of claim 1 wherein the ion exchanging sites of Component A are anion exchanging sites, those of Component B are cation exchanging sites, and the ions separated thereby are cations.

7. The process of claim 6 wherein the ion exchanging sites of Component B are chelating sites which are attracted to the anion exchanging sites of Component A and the ions separated thereby are cations.

8. The process of claim 1 wherein the ion exchanging sites of Component A are cation exchanging sites, those of Component B are anion exchanging sites, and the ions separated thereby are anions.

9. The process of claim 8 wherein Component A comprises finely divided particles of about 35 to about 75 microns particle size whose ion exchanging sites are strong acid cation exchanging sites.

10. The process of claim 9 wherein the ion exchanging sites of Component B are strong base anion exchanging sites.

11. The process of claim 10 wherein Component B particles are of from about 0.6 to about 1.8 micron median diameter.

12. The process of claim 10 wherein Component B particles are latex particles.

13. The process of claim 1 wherein Component B particles have ion exchanging sites substantially throughout the entirety of a majority of the Component B particles.

14. The process of claim 1 wherein Component B particles are latex particles.

15. The process of claim 1 wherein the synthetic resin of Component A and the synthetic resin of Component B both comprise a poly(vinylaromatic) resin.

16. The process of claim 1 wherein Component A comprises finely divided particles of a sulfonated poly(vinylaromatic) resin, said particles having about 35 microns to about 75 microns particle size and Component B comprises quaternary ammonium poly(vinylaromatic) resin particles of from about 0.6 micron to about 1.8 microns median diameter.

* * * * *

UNITED STATES PATENT AND TRADEMARK OFFICE
CERTIFICATE OF CORRECTION

PATENT NO. : 4,252,644  
DATED : February 24, 1981  
INVENTOR(S) : Hamish Small and Timothy S. Stevens It is certified that error appears in the above-identified patent and that said Letters Patent are hereby corrected as shown below:

Col. 1, line 24, "laye" should read --layer--.

Col. 1, line 57, "patticle" should read --particle--.

Col. 2, line 48, "substrate" should read --substrate,--.

Col. 3, line 62, "0.1 about" should read --0.1 to about--.

Col. 4, line 12, "by" should read --be--.

Col. 4, line 52, "purpose" should read --purposes--.

Col. 5, line 67, "particle" should read --particles--.

Col. 7, line 57, "Embodiment" should read --Embodiments--.

Col. 9, line 20, "Anel" should read --Angel--.

Col. 9, line 62, "HClwas" should read --HCl was--.

Col. 9, line 66, "HCL" should read --HCl--.

Col. 10, line 8, "$K^{30}:Na^{30}=1.5.$" should read --$K^+:Na^+=1.5.$--.

Col. 10, line 49, after the word "and" insert -- $Cl^-$ was --.

Col. 11, line 4, "Example" should read --Examples--.

Col. 11, line 37, "a" should read --the--.

UNITED STATES PATENT AND TRADEMARK OFFICE
CERTIFICATE OF CORRECTION

PATENT NO. : 4,252,644
DATED : February 24, 1981
INVENTOR(S) : Hamish Small and Timothy S. Stevens It is certified that error appears in the above-identified patent and that said Letters Patent are hereby corrected as shown below:

Col. 11, line 40, "MSC-lcation" should read --MSC-1 cation--.

Col. 11, line 68, "$SO_4$--peak" should read --$SO_4^=$ peak--.

Col. 12, line 19, after "0.002M," insert --0.001M--.

Col. 12, line 20, "emplyed" should read --employed--.

Col. 12, line 28, "$NO_3$-1.2;" should read --$NO_3^-$:$NO_2^-$ 1.2;--.

Col. 12, line 58, "pased" should read --passed--.

Col. 12, line 59, "and9" should read --and 9--.

Col. 13, line 63, "$D\sqrt[3]{10}$" should read --$D_m\sqrt[3]{10}$--.

Col. 13, line 64, "compostions" should read --compositions--.

Col. 13, line 68, "bi." should read --bi- --.

Col. 14, line 24 in Table I, "Centifuged" should read --Centrifuged--.

Col. 14, line 53, "of" should read --to--.

Col. 14, line 56, "reslution" should read --resolution--.

Col. 15, line 20, "selectively" should read --selectivity--.

UNITED STATES PATENT AND TRADEMARK OFFICE
CERTIFICATE OF CORRECTION

PATENT NO. : 4,252,644

DATED : February 24, 1981

INVENTOR(S) : Hamish Small and Timothy S. Stevens

It is certified that error appears in the above-identified patent and that said Letters Patent are hereby corrected as shown below:

Col. 17, line 21, after the word "comprising" insert the phrase --a composition of matter for exchanging ions comprising--.

Signed and Sealed this

Twenty-fifth Day of August 1981

[SEAL]

Attest:

Attesting Officer

GERALD J. MOSSINGHOFF

Commissioner of Patents and Trademarks